United States Patent [19]

Nita et al.

[11] Patent Number: 5,519,141

[45] Date of Patent: May 21, 1996

[54] INTERMOLECULAR COMPOUND AND PRODUCTION METHOD THEREOF

[75] Inventors: Kyoji Nita; Hideki Kanno; Mayumi Odagiri, all of Koshigaya; Nobuyasu Takahashi, Tokyo, all of Japan

[73] Assignee: Junsei Chemical Co., Ltd., Tokyo, Japan

[21] Appl. No.: 277,590

[22] Filed: Jul. 20, 1994

[30] Foreign Application Priority Data

Jul. 21, 1993 [JP] Japan .................................. 5-180299

[51] Int. Cl.$^6$ .................................................. C07D 275/03
[52] U.S. Cl. .................................................. 548/213
[58] Field of Search .................................................. 548/213

[56] References Cited

FOREIGN PATENT DOCUMENTS

| | | |
|---|---|---|
| 571313 | 11/1993 | European Pat. Off. . |
| 21240 | 2/1971 | Japan . |
| 53201 | 3/1986 | Japan . |
| 22701 | 1/1987 | Japan . |
| 190602 | 7/1989 | Japan . |
| 316564 | 11/1992 | Japan . |
| 5105604 | 4/1993 | Japan . |
| 105604 | 4/1993 | Japan . |

OTHER PUBLICATIONS

J. Magn. Reson. (1976), 21(3), 445–56.
Hsieh, et al., "Nitrogen–14 NQR Spectra of Glyoximes and Bis(glyoximato)–metal Complexes", Journal Of Magnetic Resonance 21, 445–456 (1976).

*Primary Examiner*—Robert Gerstl
*Attorney, Agent, or Firm*—Sherman and Shalloway

[57] ABSTRACT

An intermolecular compound of dichloroglyoxime and 5-chloro-2-methyl-3-isothiazolone as a novel compound obtained by reacting dichloroglyoxime with 5-chloro-2-methyl-3-isothiazolone. The intermolecular compound is useful as an antibacterial agent.

5 Claims, 6 Drawing Sheets

INTERMOLECULAR COMPOUND AND PRODUCTION METHOD THEREOF

BACKGROUND OF THE INVENTION

This invention relates to a novel intermolecular compound, that is, an intermolecular compound of dichloroglyoxime and 5-chloro-2-methyl-3-isothiazolone, which is useful as an antibacterial agent, and a production method thereof.

DESCRIPTION OF THE PRIOR ART

In water recirculation systems such as a cooling water system of various industrial facilities or pulp and paper making systems, slime of varieties of bacteria, algae, fauna and flora tends to adhere, which may cause various troubles.

For example, in the cooling water system, slime of zooglea-type bacteria, algae, or molds adheres, which causes a reduction in thermal efficiency, deterioration of water flow, induced corrosion of metallic materials, or the like. In the pulp and paper making system, slime of bacteria, molds, and yeasts occurs, which mixes in the pulp slurry causing a trouble such as deterioration of product quality or breakage of sheet. Further, on the intake gate or the inner wall of cooling water pipes in thermal power plants and ironworks, organisms such as seawater algae and bacteria, mussel, and Ascidiacea tend to adhere, which cause deterioration of functions.

These adhesive organisms tend to peel off by water flow, and cause clogging of tubes of heat exchangers or strainers, resulting in deterioration of functions of the entire water systems.

Heretofore, to prevent such troubles due to slime and the like, it has been convenient and inexpensive to use a slime control agent (antibacterial agent). Antibacterial agents which are generally used include water-soluble antibacterial agents of isothiazolone type compounds. Of these compounds, 5-chloro-2-methyl-3-isothiazolone (hereinafter referred to as CMIT) is superior in antibacterial effect, and is thus widely used in various slime control agents such as for cooling water system, pulp and paper, and swimming pool, antibacterial agents, alga control agents, and mildew-proof agents.

In general, CMIT is synthesized by the following methods:

1) β-Thioketoamide is halogenated in an inert organic ester solvent such as acetate ester.
2) β-Substituted thiocyanoacrylamide is treated with an acid, and then halogenated (Japanese Patent 46-21240).

However, any of these methods does not give only CMIT, but merely a mixture with 2-methyl-3-isothiazolone (hereinafter referred to as MIT), as a by-product which has about 1/10 the antibacterial effect of CMIT, is obtained. Further, in the prior art, it is difficult to selectively isolate only CMIT from the reaction mixture, and it is obliged to use the mixture of MIT which is inferior in antibacterial effect.

CMIT, although it is superior in antibacterial effect, is very irritative to the skin, and thus must be handled with care. Further, it is difficult to maintain the antibacterial effect when used in water.

Recently, it has been attempted to selectively include CMIT, and bisphenolic compounds or those having similar structures are proposed as host compounds (Japanese Patent Laid-open Publications 1-190602, 4-316564, 62-22701, 61-53201).

The host compounds described in these literatures are superior in inclusion ability of CMIT, and the inclusion compounds are remarkably relaxed in skin irritation, and easy to handle.

However, in the inclusion compounds using these host compounds, remains and degradability of the big host compounds themselves in the system after use are a problem. Further, since the inclusion compounds have a very high releasing rate of CMIT to the water system, they cannot be applied to a system requiring a continuous effect, such as for sterilization a recirculation toilet in trains.

SUMMARY OF THE INVENTION

The inventors have conducted intensive studies to improve drawback, and found that dichloroglyoxime (hereinafter referred to as DCG), which is superior in degradability, selectively forms an intermolecular compound with CMIT, and the dissociation rate in water system of the intermolecular compound is very slow compared to known inclusion compounds, achieving the present invention. Therefore, a primary object of the present invention is to provide a novel intermolecular compound, which is useful as an antibacterial agent, and a production method thereof.

DETAILED DESCRIPTION OF THE INVENTION

The present invention is directed to an intermolecular compound between DCG of Formula (1) and CMIT of Formula (2), and to a production method of the intermolecular compound of DCG and CMIT by reacting DCG with CMIT.

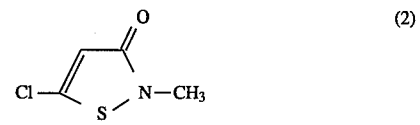

The present invention will now be described in detail.

DCG of Formula (1) used in the present invention is a compound having a very strong antibacterial effect even alone (Japanese Patent Application 3-21385). Single substance of the compound is immediately hydrolyzed in an aqueous medium above neutral to oxalic acid, and then further biodegraded. On the other hand, the compound is also known as one of the ligands of oxime-based metal complexes (Journal of Magnetic Resonance, 21, 445–456 (1976)).

CMIT of Formula (2) used in the present invention is commercially available as a main component of a water-soluble bactericide (brandname: KATHON/WT, Rohm & Haas). However, the commercial water-soluble bactericide also contains MIT as a by-product of synthesis and magnesium chloride, magnesium nitrate, or the like as a stabilizer.

CMIT as one component of the intermolecular compound of the present invention is water-soluble and strongly irritative to the skin. However, when the intermolecular compound with DCG is formed and crystallized, it becomes sparingly soluble in water, the skin irritation is relaxed, the compound is easy to handle and can be widely used as an antibacterial agent having synergetically strong bactericidal and inhibiting effects.

In the production method of the intermolecular compound of the present invention, a compound 1 is dissolved in an organic solvent, added to an aqueous solution of compound 2, and stirred for several minutes at room temperature to form the intermolecular compound of DCG and CMIT, which precipitates. The precipitate is filtered, washed, and dried to obtain a crystal. The crystal can also be recrystallized from acetonitrile or the like to enhance the purity.

Formation of the intermolecular compound can be confirmed by the following analyses.

1) IR absorption spectrum

Figure 1:
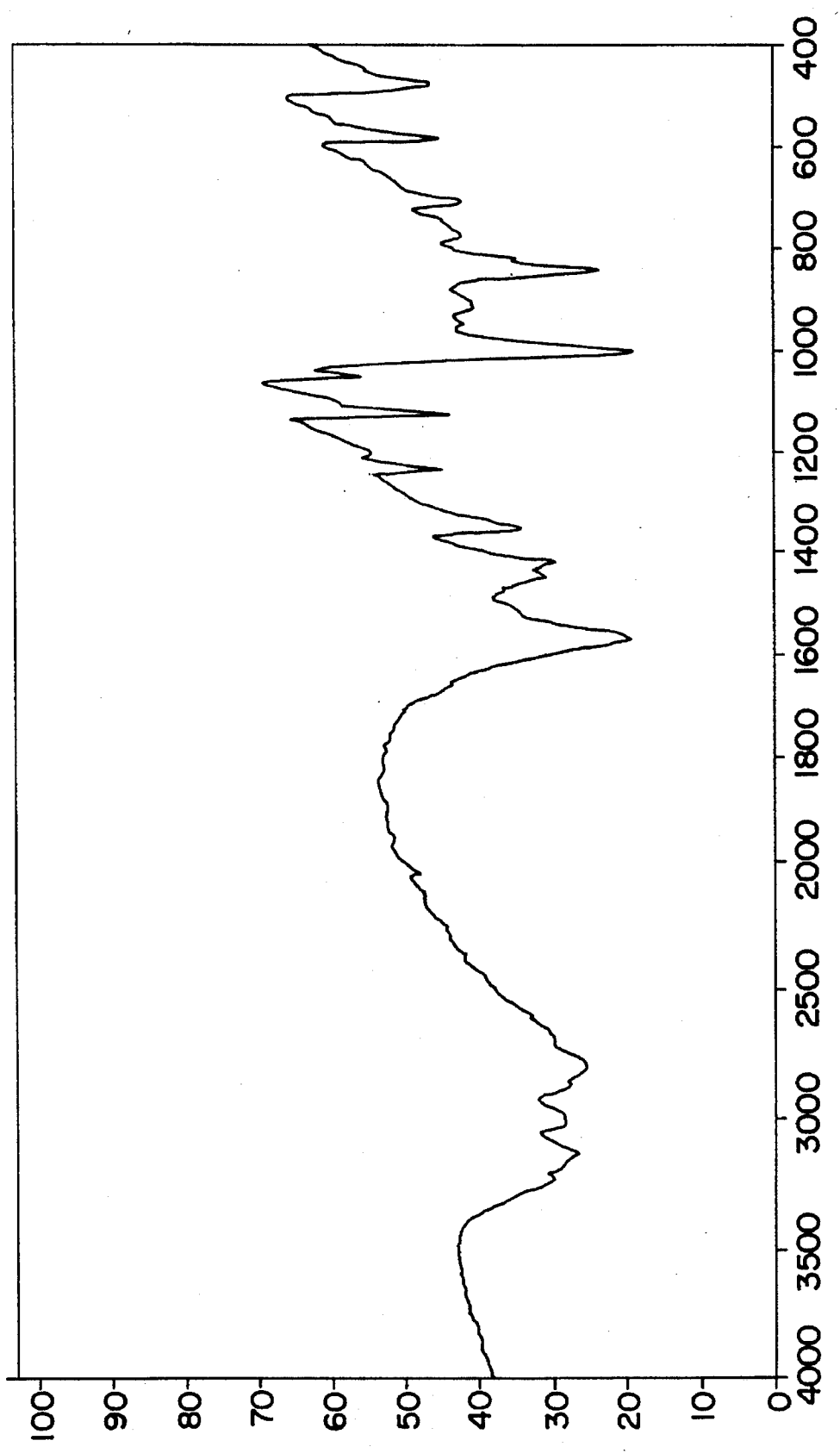
FIG. 1 is an IR spectrum of intermolecular compound X-1.
Figure 2:
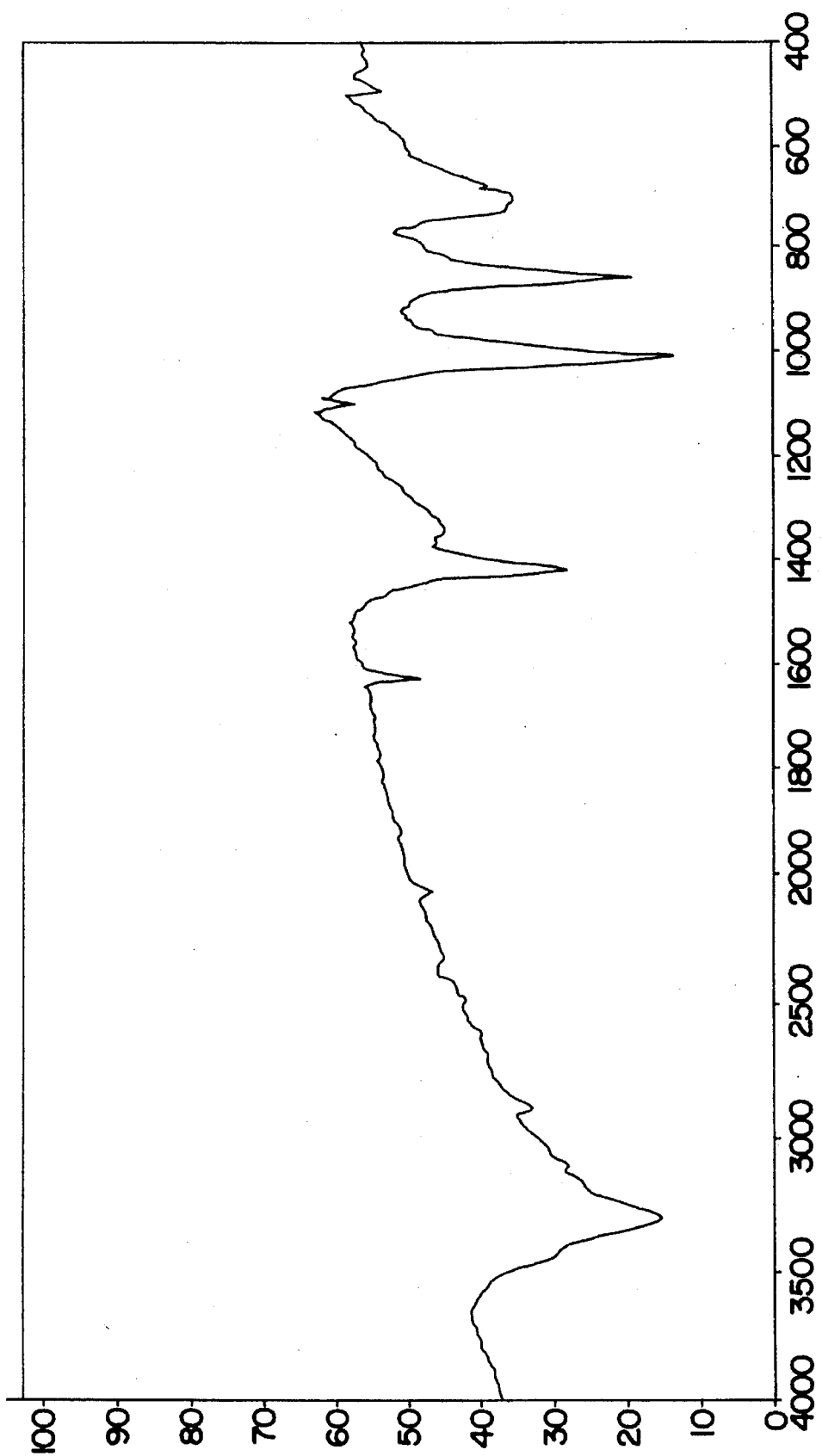
FIG. 2 is an IR spectrum of DCG.
Figure 3:
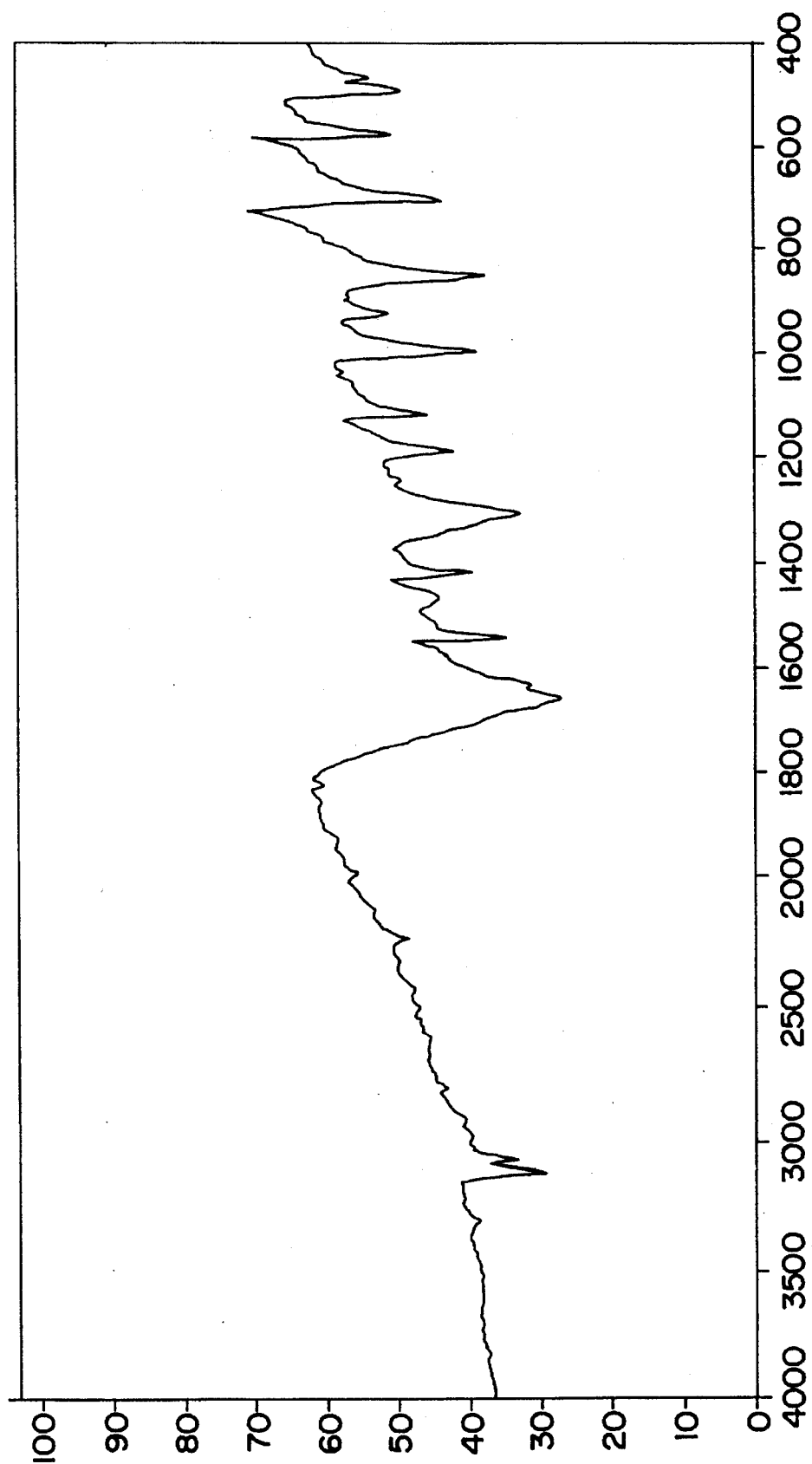
FIG. 3 is an IR spectrum of CMIT.

In measurement by the KBr tablet method of the crystal, the position of absorption wave number owing to C=O stretching vibration of CMIT was shifted from 1650 cm$^{-1}$ to 1576 cm$^{-1}$. The absorption wave number position 3272 cm$^1$ of OH stretching vibration of DCG disappeared. The results show that CMIT and DCG form a new compound (FIGS. 1 to 3).

2) UV absorption spectrum

Figure 4:
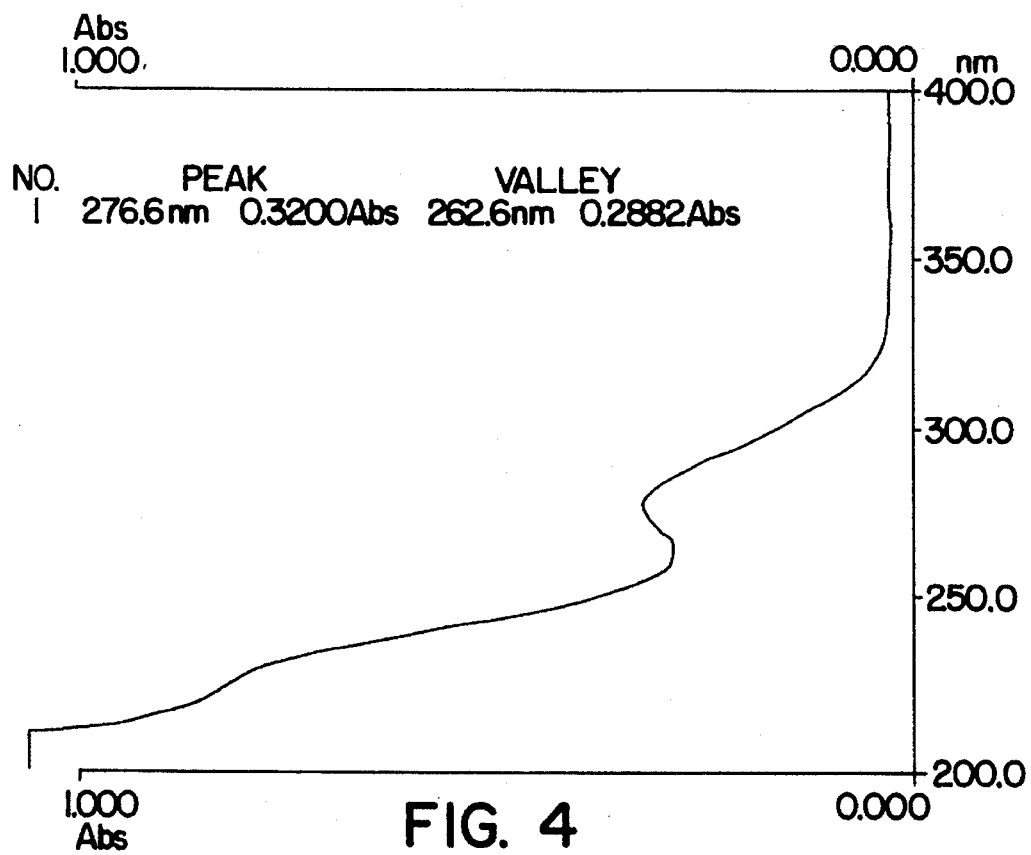
FIG. 4 is an UV spectrum of intermolecular compound X-1.
Figure 5:
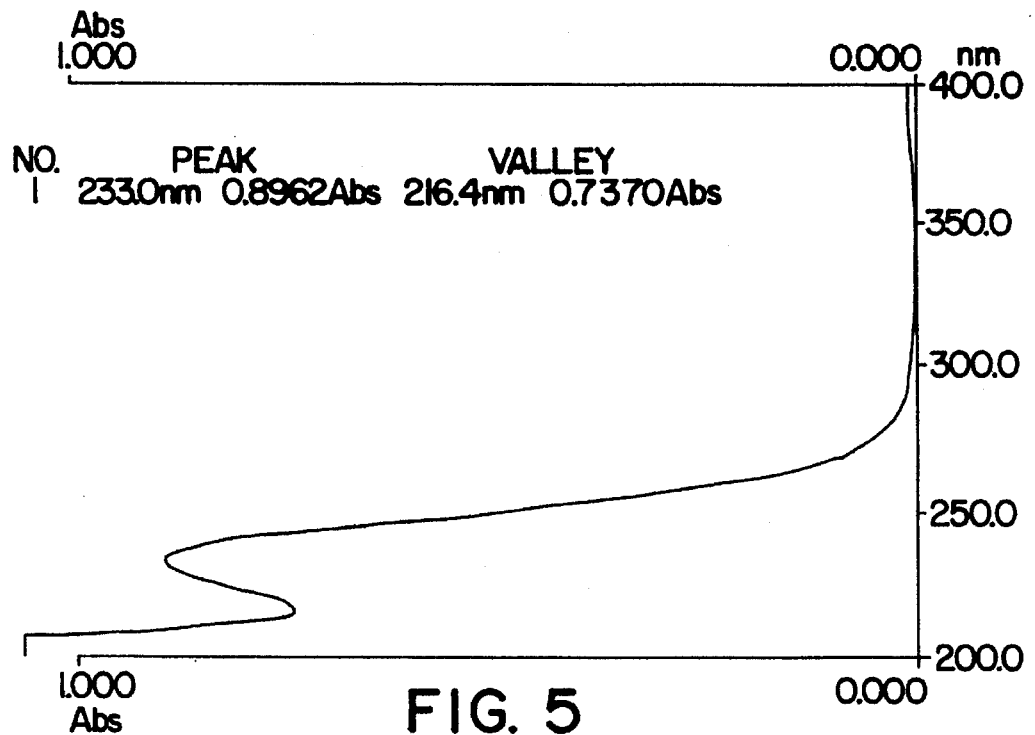
FIG. 5 is an UV spectrum of DCG.
Figure 6:
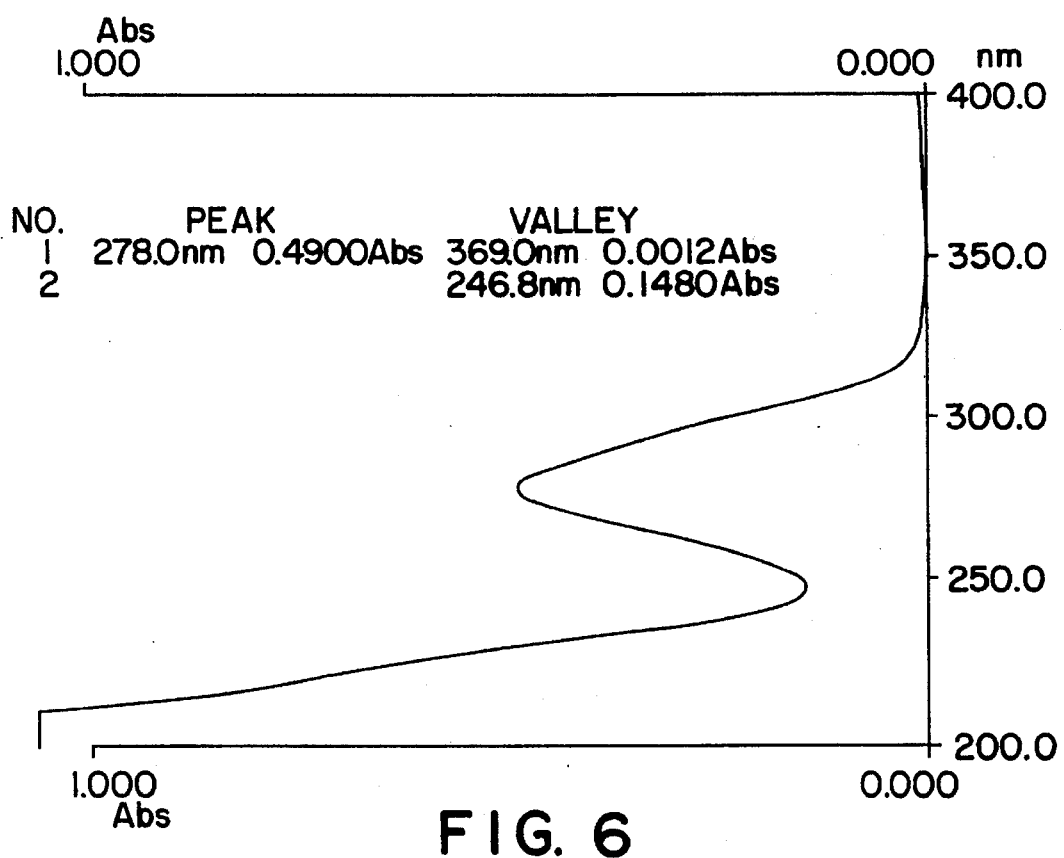
FIG. 6 is an UV spectrum of CMIT.

Spectrum of the acetonitrile solution of the intermolecular compound is a sum of spectra of acetonitrile solutions of DCG and CMIT, and shows that the intermolecular compound dissociates in the organic solution (FIGS. 4 to 6).

3) High-speed liquid chromatography

Figure 7:
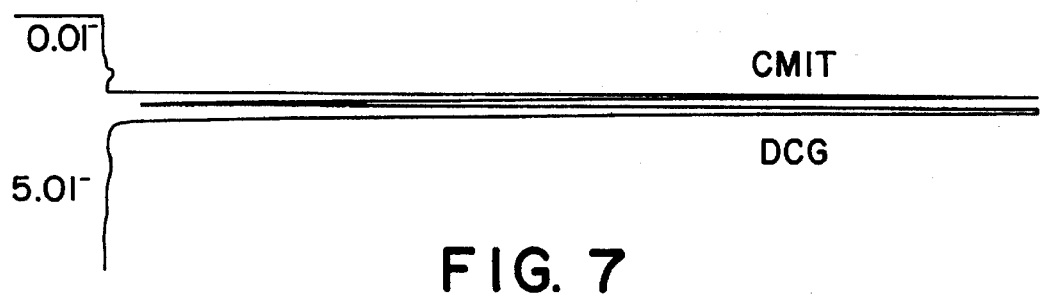
FIG. 7 is an HPLC chromatogram of intermolecular compound X-1.

Individual calibration curves of DCG and CMIT were prepared, and the intermolecular compound was analyzed on the basis of the calibration curves to calculate the molar ratio of the components. Thus, formation of the intermolecular compound, the molar ratio, and its dissociation were confirmed (FIG. 7).

4) Atomic absorption photometer

Absence of magnesium was confirmed. Therefore, the present invention is represented by the following equation.

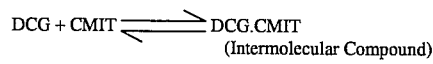

$$DCG + CMIT \rightleftharpoons DCG.CMIT$$
(Intermolecular Compound)

In the method of the present invention, even when a water-soluble bactericide (KATHON WT) is used as the raw material CMIT, only the effective component is selectively combined to obtain the intermolecular compound. The molar ratio of DCG and CMIT is constantly 1:1. In the above reaction, MIT, which exists in the water-soluble bactericide containing by-products and the like, does not combine, but only CMIT having a strong bactericidal effect advantageously combines. Thus, these compounds are preferable as component compounds of the intermolecular compound.

Figure 8:
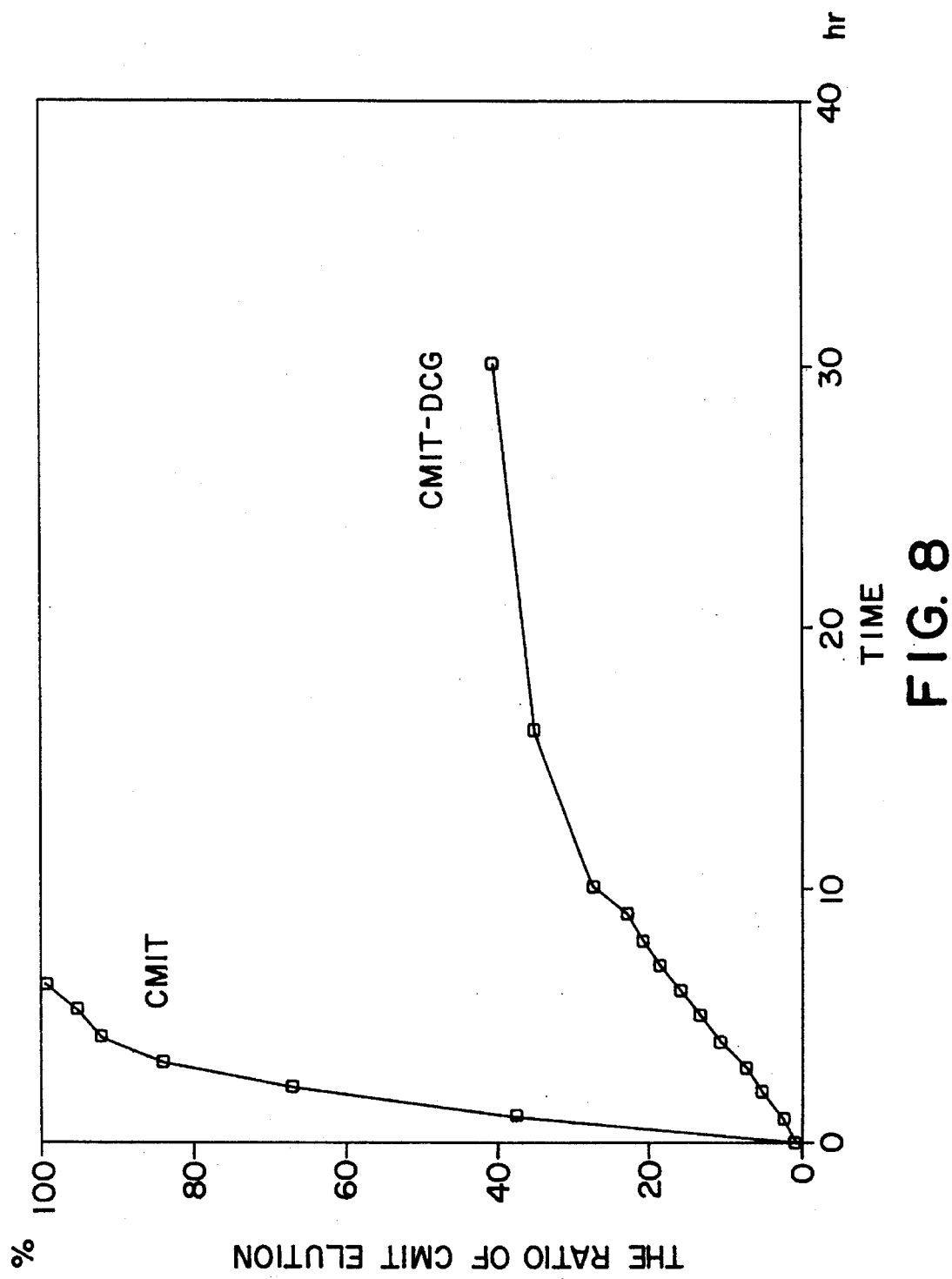
FIG. 8 is a graph showing a releasing curve obtained by releasing test of CMIT alone of a sample X-1.

The intermolecular compound of the present invention is a time-release antibacterial agent, which releases DCG and CMIT in water, providing an effect as a bactericide (FIG. 8). Therefore, it can be used by various conventional methods known in the art for adding known water treatment agents such as bactericides to waste water. Examples of the method are as follows:

1) The intermolecular compound in powder form is added continuously or intermittently at a predetermined rate to waste water.
2) A molding of the intermolecular compound, such as tablets or granules, which is solid at ordinary temperature is filled in a column, and waste water is passed through the column.
3) The intermolecular compound is put into a container, which is water-insoluble but water-permeable, such as a cartridge, and immersed in or floated on waste water.
4) The intermolecular compound is mixed directly or with a paint or resin, and coated on the surface of apparatus or piping which contacts with waste water.

As described above in detail, the present invention is directed to an intermolecular compound of DCG and CMIT, which has properties as follows:

1) Since the intermolecular compound is sparingly soluble in water, it can slowly release water-soluble CMIT to the water medium.
2) DCG also provides an antibacterial activity by dissociation of the intermolecular compound in water medium.
3) The intermolecular compound has a small dissociation rate in water medium, and the released components are small in amounts, however, since the components are very high in antibacterial activity and long in dissociation time, the antibacterial activity can be maintained for a long time (FIG. 8).
4) After dissociation, the individual molecules are decomposed after providing antibacterial effects, and become environmentally safe.
5) Since the strongly skin irritant CMIT forms the intermolecular compound with DCG, the irritation is relaxed and the components can be used safely.
6) The unstable compound CMIT is stabilized by the formation of the intermolecular compound.
7) When the intermolecular compound can be dissolved in an organic solvent, it immediately dissociates to give a known antibacterial agent which has a synergetic effect of DCG and CMIT (Japanese Patent Laid-open Publication 5-105604).

DETAILED DESCRIPTION OF PREFERRED EMBODIMENTS

While the present invention will now be described further in detail with reference to the examples, it is not intended to limit the invention to these particular examples.

EXAMPLE 1

To an aqueous solution of 2.0 g (13.4 mmole) of purified CMIT crystal and 58 ml of water, a solution of 2.0 g (12.7 mmole) of pure DCG and 20 ml of ethyleneglycol was added, and mixture stirred to precipitate a white crystal. After the reaction mixture was allowed to stand at 4° C. for 16 hours, the precipitate was filtered and vacuum dried at room temperature to obtain 2.87 g (71.2% yield) of white crystal.

The crystal was recrystallized from acetonitrile to obtain a white crystal (X-1), which had a melting point of 128.5° to 130.5° (solidify) to 133° C. (dec).

EXAMPLE 2

To a solution including 26.5 g of KATHON WT and 100 ml of water, a solution of 2.5 g of DCG and 25 ml of methanol was added, and stirred to precipitate a white crystal. After the reaction mixture was allowed to stand at 4° C. for 16 hours, the precipitate was filtered and vacuum dried at room temperature to obtain 3.55 g (71% yield) of white crystal (X-2).

EXAMPLE 3

To a solution including 26.5 g of KATHON WT and 100 ml of water, a solution of 2.5 g of DCG and 25 ml of ethanol was added, and stirred to precipitate a white crystal. After the reaction mixture was allowed to stand at 4° C. for 16 hours, the precipitate was filtered and vacuum dried at room temperature to obtain 2.81 g (56.2% yield) of white crystal (X-3).

EXAMPLE 4

To a solution including 26.5 g of KATHON WT and 100 ml of water, a solution of 2.5 g of DCG and 10 ml of ethyleneglycol was added, and stirred to precipitate a white crystal. After the reaction mixture was allowed to stand at 4° C. for 16 hours, the precipitate was filtered and vacuum dried at room temperature to obtain 3.81 g (76.2% yield) of white crystal (X-4).

EXAMPLE 5

To a solution including 26.5 g of KATHON WT and 100 ml of water, a solution of 2.5 g of DCG and 20 ml of N,N-dimethylformamide was added, and stirred to precipitate a white crystal. After the reaction mixture was allowed to stand at 4° C. for 16 hours, the precipitate was filtered and vacuum dried at room temperature to obtain 1.89 g (37.4% yield) of white crystal (X-5).

Note) Analytical values of the water-soluble bactericidal agent (KATHON WT) used in Examples 2 to 5 are:

CMIT: 9.44%

MIT: 3.53%

The remnant is magnesium chloride+magnesium nitrate+water:

Analytical results of the thus obtained intermolecular compounds (X-1 to X-5) of the present invention are shown in Table 1.

TABLE 1

| Sample | Reaction solvent | CMIT/DCG (molar ratio) |
|---|---|---|
| Example 1 | X-1 | Ethylene glycol + water (recrystallization) | 1.01 |
| Example 2 | X-2 | Methanol + water | 1.03 |
| Example 3 | X-3 | Ethanol + water | 1.02 |
| Example 4 | X-4 | Ethylene glycol + water | 1.02 |
| Example 5 | X-5 | N,N-dimethylformamide + water | 1.03 |

Further, as a CMIT releasing test, sample X-1 and CMIT alone were individually put in a cellulose-based dialytic membrane tube so that 10 mg equivalent of CMIT was contained, water was added, the tube was closed and immersed in 1 liter of pure water, and releasing amount of CMIT after a predetermined time was measured to determine the releasing rate over time. The test results are shown in FIG. 8.

It is evident from FIG. 8 that CMIT alone is released within 6 hours from immersion of the dialytic membrane tube and, on the contrary, sample X-1 shows an appropriate time-release rate of 40% in 30 hours.

As described above, the intermolecular compound of the present invention is a novel intermolecular compound of CMIT and DCG which is effective as an antibacterial agent, and has the following features.

1) High skin irritation of CMIT can be relaxed by forming the intermolecular compound with DCG.

2) Since the intermolecular compound is solid at ordinary temperature, it can be prepared to tablets and is thus very easy to handle.

3) The effective component CMIT is released in water medium at an appropriate rate.

4) The unstable CMIT is stabilized by the formation of the intermolecular compound.

5) DCG itself also has a very strong bactericidal effect, and has a synergetic effect with CMIT.

Therefore, the present invention provides a novel intermolecular compound which is effective as a bactericidal agent having an appropriate time-release effect and easy to handle, and a production method thereof. Therefore, the present invention can be used to good advantage particularly in water treatment applications.

What is claimed is:

1. A solid composition comprising an intermolecular compound of dichloroglyoxime of formula (1)

and 5-chloro-2-methyl-3-isothiazolone of formula (2)

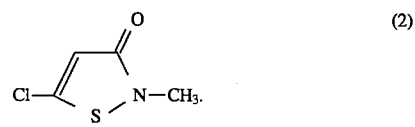

2. A method for producing the solid composition of claim 1 comprising mixing an organic solvent solution of dichloroglyoxime with an aqueous solution of 5-chloro-2-methyl-3-isothiazolone; and crystallizing said solid composition as a water-insoluble precipitate.

3. The method according to claim 2, wherein said organic solvent is selected from the group consisting of methanol, ethanol, ethylene glycol and N,N-dimethylformamide.

4. The method according to claim 2, wherein said aqueous solution of 5-chloro-2-methyl-3-isothiazolone comprises 5-chloro-2-methyl-3-isothiazolone, 2-methyl-3-isothiazolone, a metal salt and water.

5. The method according to claim 4, wherein said metal salt is selected from the group consisting of nitrate, chloride and mixtures thereof.

* * * * *